US012698339B2

(12) United States Patent
Yaguchi et al.

(10) Patent No.:  US 12,698,339 B2
(45) Date of Patent:  *Aug. 4, 2026

(54) ANTI-GLYPICAN-1-IMMUNIZING ANTIGEN RECEPTOR

(71) Applicants: Keio University, Tokyo (JP); Iwate Medical University, Iwate (JP)

(72) Inventors: Tomonori Yaguchi, Tokyo (JP); Kenji Morii, Tokyo (JP); Yutaka Kawakami, Tokyo (JP); Daiki Kato, Tokyo (JP); Tetsuji Naka, Ibaraki (JP); Satoshi Serada, Ibaraki (JP); Minoru Fujimoto, Ibaraki (JP)

(73) Assignees: Keio University, Tokyo (JP); Iwate Medical University, Iwate (JP)

( * ) Notice: Subject to any disclaimer, the term of this patent is extended or adjusted under 35 U.S.C. 154(b) by 1003 days.

This patent is subject to a terminal disclaimer.

(21) Appl. No.: 17/846,446

(22) Filed: Jun. 22, 2022

(65) Prior Publication Data

US 2022/0356265 A1  Nov. 10, 2022

Related U.S. Application Data

(62) Division of application No. 15/739,580, filed as application No. PCT/JP2016/068924 on Jun. 24, 2016, now Pat. No. 11,370,845.

(30) Foreign Application Priority Data

Jun. 24, 2015  (JP) ................................. 2015-127001

(51) Int. Cl.
| | |
|---|---|
| *C07K 16/30* | (2006.01) |
| *A61K 31/7105* | (2006.01) |
| *A61K 38/00* | (2006.01) |
| *A61K 40/11* | (2025.01) |
| *A61K 40/31* | (2025.01) |
| *A61K 40/42* | (2025.01) |
| *A61K 48/00* | (2006.01) |
| *A61P 1/00* | (2006.01) |
| *A61P 35/00* | (2006.01) |
| *C07K 14/705* | (2006.01) |
| *C12N 5/0783* | (2010.01) |

(52) U.S. Cl.
CPC .......... *C07K 16/30* (2013.01); *A61K 31/7105* (2013.01); *A61K 38/00* (2013.01); *A61K 40/11* (2025.01); *A61K 40/31* (2025.01); *A61K 40/4261* (2025.01); *A61K 48/00* (2013.01); *A61P 1/00* (2018.01); *A61P 35/00* (2018.01); *C07K 14/70503* (2013.01); *C07K 14/7051* (2013.01); *C07K 14/70521* (2013.01); *C07K 16/3046* (2013.01); *C12N 5/0636* (2013.01); *A61K 2239/31* (2023.05); *A61K 2239/38* (2023.05); *A61K 2239/50* (2023.05); *C07K 2319/02* (2013.01); *C07K 2319/03* (2013.01)

(58) Field of Classification Search
CPC .............. C07K 16/30; C07K 14/70503; C07K 14/7051; C07K 14/70521; C07K 16/3046; C07K 2319/02; C07K 2319/03; C07K 2319/33; A61K 31/7105; A61K 38/00; A61K 40/11; A61K 40/31; A61K 40/4261; A61K 48/00; A61K 2239/31; A61K 2239/38; A61K 2239/50; A61P 1/00; A61P 35/00; C12N 5/0636; C12N 2510/00

See application file for complete search history.

(56) References Cited

U.S. PATENT DOCUMENTS

| | | | |
|---|---|---|---|
| 9,783,591 | B2 | 10/2017 | June et al. |
| 2012/0003219 | A1 | 1/2012 | Lu et al. |
| 2016/0215261 | A1 | 7/2016 | Li et al. |
| 2017/0066836 | A1 | 3/2017 | Naka et al. |

FOREIGN PATENT DOCUMENTS

| | | |
|---|---|---|
| JP | 2010-526766 A | 8/2010 |
| JP | 2015-509716 A | 4/2015 |
| WO | 2014/180306 A1 | 11/2014 |
| WO | 2015/098112 A1 | 3/2017 |

OTHER PUBLICATIONS

International Search Report from PCT/JP2016/068924 (mailed Sep. 13, 2016).
Written Opinion from PCT/JP2016/068924 (mailed Sep. 13, 2016).

(Continued)

*Primary Examiner* — Titilayo Moloye
(74) *Attorney, Agent, or Firm* — Merchant & Gould P.C.

(57) ABSTRACT

The purpose of the present invention is to produce a chimeric antigen receptor (CAR) specific to glypican-1 (GPC-1) and to treat squamous cell carcinoma with genetically modified cells capable of expressing the CAR. The present invention provides: a chimeric antigen receptor for use in the treatment and/or prevention of squamous cell carcinoma, said chimeric antigen receptor comprising an extracellular domain capable of binding to GPC-1, a transmembrane domain and one or multiple intracellular domains, wherein at least one of the intracellular domains is an intracellular domain containing a primary cytosolic signaling sequence or an intracellular domain containing both a primary cytosolic signaling sequence and a secondary cytosolic signaling sequence; a genetically modified cell capable of expressing the chimeric antigen receptor; and a cell preparation containing the cell.

12 Claims, 7 Drawing Sheets

Specification includes a Sequence Listing.

(56)                    References Cited

OTHER PUBLICATIONS

Poli et al., "Proteoglycans as potential markers of the biological behaviour of head and neck carcinomas: Interim results of a multicenter Italian project," Oral Oncology, vol. 47, Supp. 1, S38 (2011).

Lu Xiping et al., "Hedgehog signaling pathway mediated Gpc1 regulation on the proliferation of neuroglioma cells", Journal of Chongqing Medical University, vol. 39, No. 11: 1647-1652 (2014) with English Abstract.

S.L. Maude et al., "CD19-targeted chimeric antigen receptor T-cell therapy for acute lymphoblastic leukemia", Acute Lymphoblastic Leukemia, Blood, vol. 125 (26): 4017-4023 (2015).

S.A. Grupp et al., "Chimeric Antigen Receptor-Modified T Cells for Acute Lymphoid Leukemia", The New England Journal of Medicine, 368;16: 1509-1518 (2013).

J.N. Kochenderfer et al., "B-cell depletion and remissions of malignancy along with cytokine-associated toxicity in a clinical trial of anti-CD19 chimeric-antigen-receptor-transduced T cells", Blood, 119(12): 2809-2720 (2012).

Cor H.J. Lamers et al., "Treatment of Metastatic Renal Cell Carcinoma With CAIX CAR-engineered T cells: Clinical Evaluation and Management of On-target Toxicity", Clinical Management of CAIX CAR On-target Toxicity, www.moleculartherapy.org vol. 21(4): 904-912 (2013).

J.N. Kochenderfer et al., "Eradication of B-lineage cells and regression of lymphoma in a patient treated with autologous T cells genetically engineered to recognize CD19", Gene Therapy, Blood, 116(20): 4099-4102 (2010).

R.A. Morgan et al., "Case Report of a Serious Adverse Event Following the Administration of T Cells Transduced With a Chimeric Antigen Receptor Recognizing ERBB2", Molecular Therapy, 18(4): 843-851 (2010).

B.J. Cameron et al., "Identification of a Titin-Derived HLA-A1-Presented Peptide as a Cross-Reactive Target for Engineered MAGE A3-Directed T Cells", Sci Transl Med. Author manuscript; available in PMC: 1-24 (2018).

R.O. Carpenter et al., "B-cell Maturation Antigen Is a Promising Target for Adoptive T-cell Therapy of Multiple Myeloma", Clin Cancer Res; 19(8): 2048-2060 (2013).

SS Kenderian et al., "CD33-specific chimeric antigen receptor T cells exhibit potent preclinical activity against human acute myeloid leukemia", Leukemia 29, 1637-1647(2015).

H. Qin et al., "Eradication of B-ALL using chimeric antigen receptor-expressing T cells targeting the TSLPR oncoprotein", Blood, 126(5): 629-639 (2015).

Cor H.J. Lamers et al., "Treatment of Metastatic Renal Cell Carcinoma With Autologous T-Lymphocytes Genetically Retargeted Against Carbonic Anhydrase IX: First Clinical Experience", Journal of Clinical Oncology, 24(13): e20-e22 (2006).

Cor H.J. Lamers et al., "Gene-modiWed T cells for adoptive immunotherapy of renal cell cancer maintain transgene-speciWc immune functions in vivo", Cancer Immunol Immunother 56:1875-1883 (2007).

Cor H.J. Lamers et al.,"Immune responses to transgene and retroviral vector in patients treated with ex vivo-engineered T cells", Blood, 117(1): 72-82 (2011).

G.P. Linette et al., "Cardiovascular toxicity and titin cross-reactivity of affinity-enhanced T cells in myeloma and melanoma", Blood, 122(6): 863-871 (2013).

R.A. Morgan et al., "Cancer regression and neurologic toxicity following anti-MAGEA3 TCR gene therapy", J Immunother 36(2): 133-151 (2013).

Whipple et al., "A KrasG12D-driven genetic mouse model of pancreatic cancer requires glypican-1 for efficient proliferation and angiogenesis", Oncogene, 2012, 31(20): 2535-2544.

Nakazawa et al., "Genetically modified T cell therapy using chimeric antigen receptor (CAR)", Shinshu Ishi, 2013, 61(4): 197-203.

ANTI-GLYPICAN-1-IMMUNIZING ANTIGEN RECEPTOR

The present application is a Divisional of U.S. patent application Ser. No. 15/739,580, filed Dec. 22, 2017, which is a National Stage Application under 35 U.S.C. § 371 of International Application No. PCT/JP2016/068924 filed Jun. 24, 2016, which claims the benefit of priority to Japanese Patent Application No. 2015-127001 filed Jun. 24, 2015, the disclosures of all of which are hereby incorporated by reference in their entireties.

SEQUENCE STATEMENT

This application contains a Sequence Listing, which has been submitted electronically in ASCII format and is hereby incorporated by reference in its entirety. Said ASCII copy, created and filed in PCT/JP2016/068924, updated on Jun. 14, 2022, is named Seq_Listing.txt and is 4,168 bytes (4.1 KB) in size.

TECHNICAL FIELD

The present invention relates to a chimeric antigen receptor (CAR) specific to glypican-1 (GPC-1) and nucleic acid encoding the same, to genetically modified cells that express the CAR, and to a method and cell preparation for treatment and/or prevention of squamous cell carcinoma using the cells.

BACKGROUND

Squamous cell carcinoma is a commonly appearing form of cancer, and is known to be a highly invasive and metastatic cancer. Squamous cell carcinoma has a relatively high relapse rate and a considerably high mortality rate. While squamous cell carcinoma can be diagnosed by biopsy, it is typically not as distinct as basal cell carcinoma or melanoma, and its detection and diagnosis are difficult. The conventional treatment methods, namely surgery, radiation therapy and chemotherapy, require continuous monitoring because of the metastatic nature of the disease. The development of different detection methods and treatment methods is therefore desired.

Research has been progressing in recent years with the aim of treating progressive stage cancer by inducing T cells to recognize cancer cells. Antibody treatment is also being conducted using antibodies for molecules specifically expressed by cancer cells, but therapy by antibodies alone requires frequent administration, while the cytotoxic effect on cancer cells is also known to be relatively weak.

Treatment methods also exist that use CAR-T cells, prepared by creating antibodies for molecules specifically expressed by cancer cells and transferring the genes for the antibody variable regions into T cells (NPL 1). Anti-CD19-CAR-T cells have already been shown to exhibit a dramatic clinical effect, mainly against lymphatic leukemia (PTL 1). However, CAR-T cells have only actually exhibited an adequate clinical effect for treatment of lymphatic leukemia when using the anti-CD19-CAR-T cells mentioned above. No reports exist of genetically-modified T cells for CAR-T cell therapy against solid tumors.

CITATION LIST

Patent Literature

[PTL 1] Japanese Patent Public Inspection No. 2015-509716

Non-Patent Literature

[NPL 1] Nakazawa, S, "Genetically-modified T cell therapy using chimeric antigen receptor (CAR)", Shinshu Ishi, 61(4):197-203, 2013

SUMMARY OF INVENTION

Technical Problem

In light of the problems of the prior art described above, it is an object of the present invention to provide a nucleic acid sequence that can be used in a method of CAR-T therapy for solid tumors such as squamous cell carcinoma, genetically-modified T cells containing the nucleic acid sequence, and a method of treatment and/or prevention of squamous cell carcinoma.

Solution to Problem

The present inventors have previously found that glypican-1 (GPC-1) is specifically expressed in squamous cell carcinomas such as esophageal cancer, lung cancer and cervical cancer, which are solid tumors, and have created an anti-GPC-1 antibody (WO2015/098112). In addition, we have succeeded in using the gene for the anti-GPC-1 antibody to create anti-GPC-1-CAR-T cells, finding that the CAR-T cells exhibit very high GPC-1-specific cytotoxicity against solid tumors, and have thereupon completed this invention.

Specifically, the present invention provides the following.

[1] Nucleic acid encoding a chimeric antigen receptor comprising an extracellular domain capable of binding to glypican-1 (GPC-1), a transmembrane domain and one or more intracellular domains, wherein at least one of the intracellular domains is an intracellular domain containing a primary cytosolic signaling sequence.

[2] Nucleic acid according to [1] above, wherein the extracellular domain capable of binding to GPC-1 includes the heavy chain variable region (VH) and light chain variable region (VL) of anti-GPC-1 antibody.

[3] Nucleic acid according to [2] above, wherein the nucleotide sequence encoding the heavy chain variable region of anti-GPC-1 antibody includes the nucleotide sequence listed as SEQ ID NO: 1 or a nucleotide sequence with at least 95% identity therewith and having the same function, and the nucleotide sequence encoding the light chain variable region includes the nucleotide sequence listed as SEQ ID NO: 2 or a nucleotide sequence with at least 95% identity therewith and having the same function.

[4] Nucleic acid according to any one of [1] to [3] above, wherein the primary cytosolic signaling sequence contains an immunoreceptor tyrosine-based activation motif (ITMA).

[5] Nucleic acid according to [4] above, wherein the intracellular domain containing the ITAM is derived from CD3ζ, FcRγ, FcRβ, CD3γ, CD3δ, CD3ε, CD5, CD22, CD79a, CD79b or CD66d.

[6] Nucleic acid according to any one of [1] to [5] above, wherein the chimeric antigen receptor further includes one or more identical or differing intracellular domains containing a secondary cytosolic signaling sequence.

[7] Nucleic acid according to [6] above, wherein the intracellular domain containing the secondary cytosolic signaling sequence is located at the N-terminal end of the intracellular domain containing the primary cytosolic signaling sequence.

[8] Nucleic acid according to [6] or [7] above, wherein the intracellular domain containing the secondary cytosolic signaling sequence is derived from CD2, CD4, CD5, CD8α, CD8β, CD28, CD134, CD137, ICOS and/or CD154.

[9] A chimeric antigen receptor encoded by nucleic acid according to any one of [1] to [8] above.

[10] A vector containing nucleic acid according to any one of [1] to [8] above.

[11] Cells expressing a chimeric antigen receptor, having a gene transferred using a vector according to [10] above.

[12] Cells according to [11] above, wherein the cells are T cells or a cell population including T cells.

[13] A cell preparation containing cells according to [12] above, for treatment and/or prevention of a solid tumor expressing GPC-1.

[14] A cell preparation according to [13] above, wherein the solid tumor is squamous cell carcinoma.

[15] A medical composition comprising nucleic acid according to any one of [1] to [8] above, a chimeric antigen receptor according to [9], a vector according to [10] or cells according to [11] or [12], and a medically acceptable excipient.

[16] A medical composition according to [15] above, for treatment and/or prevention of a solid tumor expressing GPC-1.

[17] A medical composition according to [16] above, wherein the solid tumor is squamous cell carcinoma.

[18] The use of nucleic acid according to any one of [1] to [8] above, a chimeric antigen receptor according to [9], a vector according to [10] or cells according to [11] or [12], for production of a drug for treatment and/or prevention of a solid tumor expressing GPC-1.

[19] The use according to [18] above, wherein the solid tumor is squamous cell carcinoma.

[20] A method for treatment and/or prevention of a solid tumor expressing GPC-1, wherein nucleic acid according to any one of [1] to [8] above, a chimeric antigen receptor according to [9], a vector according to [10], cells according to [11] or [12], a cell preparation according to [13] or [14] or a medical composition according to any one of [15] to [17] is administered to an individual in need of treatment.

[21] The method according to [20] above, wherein the solid tumor is squamous cell carcinoma.

Advantageous Effects of Invention

According to the invention there is provided a chimeric antigen receptor useful in the field of adoptive immunogene therapy targeting GPC-1 antigen for squamous cell carcinoma, nucleic acid encoding the chimeric antigen receptor, and cells expressing the chimeric antigen receptor. Cells having the transferred chimeric antigen receptor of the invention exhibit high specificity and cytotoxicity against squamous cell carcinoma cells.

DESCRIPTION OF EMBODIMENTS

Figure 1:
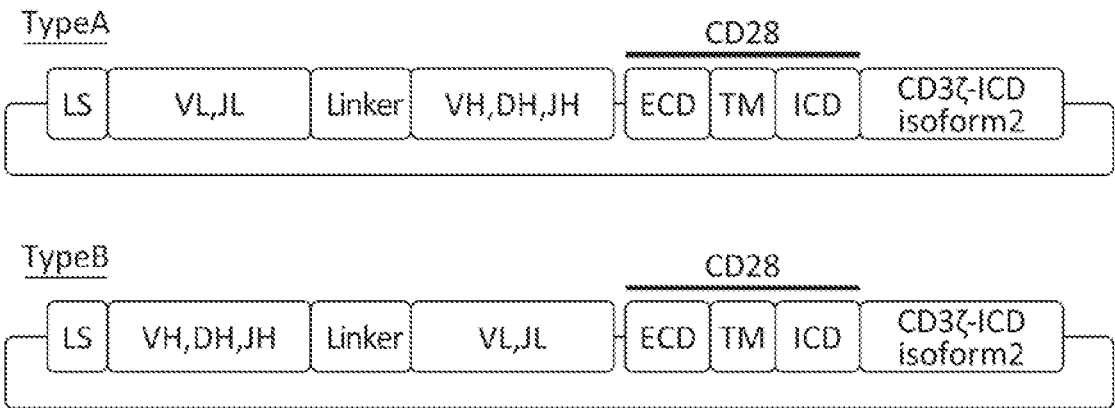
FIG. 1 shows the structure of a vector incorporating an immunogen receptor. LS: CD8α chain-derived lead sequence (SEQ ID NO: 5), Linker: (Gly4Ser)-3 linker, CD28: human CD28-derived, CD3ζ-ICD: human-derived CD3ζ intracellular domain (including the stop codon).

The present invention provides chimeric antigen receptor (CAR)-T cells for treatment of squamous cell carcinoma specifically expressing glypican-1 (GPC-1), and relates to a method of immunotherapy using the cells. The term "chimeric antigen receptor T cells" (hereunder also referred to simply as "CAR-T cells") means T cells expressing a chimeric antigen receptor (CAR). CAR is a general term encompassing chimeric proteins having, for example, a single-chain antibody with the variable region heavy chain (VH) and light chain (VL) of a tumor antigen-specific monoclonal antibody (scFv) bonded at the N-terminal end, and a T cell receptor (TCR)ζ chain, at the C-terminus. T cells expressing CAR, after having recognized a tumor antigen in the scFv region, transmit the recognition signal into the T cells via the ζ chain. A costimulatory domain may also be inserted between the scFv and ζ chain of an immunogen receptor for augmented activation of the T cells.

As used throughout the present specification, the term "single-chain antibody (scFv)" means a single-stranded polypeptide derived from an antibody, that retains the ability to bind antigen. An example is an antibody polypeptide having the Fv regions of the immunoglobulin heavy chain (H chain) and light chain (L chain) fragments linked via a spacer sequence, the polypeptide having been formed by recombinant DNA technology. Various methods for creating scFv are known, examples including the methods described in U.S. Pat. No. 4,694,778; Science, 242, 423-442(1988) and Nature, 334, 54454(1989).

As used throughout the present specification, the term "domain" means a region within a polypeptide that is folded into a specific structure independent from the other regions. Throughout the present specification, "domain" is used in the terms "extracellular domain", "transmembrane domain" and "intracellular domain", depending on its location in the chimeric antigen receptor molecule.

(1) Chimeric Antigen Receptor (CAR) of the Invention

The CAR of the invention comprises (i) an extracellular domain capable of binding to glypican-1 (GPC-1), (ii) a transmembrane domain and (c) at least one intracellular domain, in that order from the N-terminal end. The CAR of the invention has a high level of expression in cells, and cells expressing the CAR of the invention have a high cell growth rate and high cytokine production levels, and are highly specific for and cytotoxic against cells with CAR-binding GPC-1 antigen on the surface.

(a) Extracellular Domain

The "extracellular domain capable of binding to glypican-1 (GPC-1)" used in the CAR of the invention is a domain containing an oligo- or polypeptide that can bind to GPC-1 antigen as the target, and it typically includes the antigen-binding domain of anti-GPC-1 antibody. The domain, upon binding to and interacting with GPC-1 antigen, such as GPC-1 antigen localized on cancer cell surfaces, imparts specificity to the CAR-expressing cells. According to the invention, a particularly useful extracellular domain to be used is that of an antibody (heavy chain (H chain) and light chain (L chain)), and especially the domain that binds the antigen, such as the antibody Fab fragment and the antibody variable region (heavy chain variable region (VH) and light chain variable region (VL)). It is most preferred to use scFv. For scFv, the VH and VL may be directly linked in any desired order, or they may be indirectly linked via a spacer. The amino acid sequence and chain length of a spacer to be used for linkage of the VH and VL is not restricted, and any one may be selected with modification as appropriate. According to one specific mode, the extracellular domain to be used for the invention preferably has scFv comprising a heavy chain variable region having the amino acid sequence listed as SEQ ID NO: 3 and a light chain variable region having the amino acid sequence listed as SEQ ID NO: 4, in any desired order.

The extracellular domain of the CAR of the invention has the property of binding to GPC-1 antigen, and as mentioned above, the extracellular domain is preferably the scFv portion of anti-GPC-1 antibody. The anti-GPC-1 antibody source of the scFv to be used for the invention may be the anti-GPC-1 antibody previously created by the present inventors (PCT/JP2014/006455), or a monoclonal anti-GPC-1 antibody newly created with GPC-1 as antigen, using publicly known technology.

According to one mode, the extracellular domain to be used for the invention may also have another extracellular domain linked either directly or indirectly via a spacer to the extracellular domain having the aforementioned property of binding to GPC-1 antigen, at its C-terminal end. The other extracellular domain used may be the extracellular domain of a costimulatory molecule, as described below.

(b) Transmembrane Domain

The CAR of the invention comprises a transmembrane domain. The transmembrane domain may be derived from a natural polypeptide, or it may be one that has been artificially designed. A transmembrane domain derived from a natural polypeptide may be any desired membrane-bound or transmembrane protein (of a costimulatory molecule, for example). As used in the present specification, the term "costimulatory molecule" means a cognate binding partner on T cells, that specifically binds to a costimulatory ligand on the target cell membrane, thereby mediating a costimulatory response by T cells, such as cell proliferation, cytolytic activity or cytokine secretion. Examples of typical costimulatory molecules that may be used include the transmembrane domains of CD2, CD4, CD5, CD8α, CD8β, CD28, CD134, CD137, ICOS and CD154. An artificially designed transmembrane domain is a polypeptide consisting mainly of hydrophobic residues such as leucine and valine. Preferably, a phenylalanine-tryptophan-valine triplet is present on each end of a synthetic transmembrane domain. In some cases, a short oligopeptide linker or polypeptide linker, such as a linker that is a sequence with a length of 2 to 10 amino acids, may be situated between the transmembrane domain and the intracellular domain described below.

As one mode of the invention, the transmembrane domain used may be a transmembrane domain having a sequence from CD28 (for example, amino acid Nos. 153 to 179 of NCBI RefSeq: NP 006130.1).

The CAR of the invention may have a spacer domain situated between the extracellular domain and the transmembrane domain, or between the intracellular domain and the transmembrane domain. A spacer domain is any oligopeptide or polypeptide that performs the role of linking a transmembrane domain and an extracellular domain and/or a transmembrane domain and an intracellular domain. A spacer domain contains up to 300 amino acids, preferably 10 to 100 amino acids and most preferably 25 to 50 amino acids.

(c) Intracellular Domain

The intracellular domain to be used for the invention is a molecule capable of transferring a signal into the cell when an extracellular domain within the same molecule has bound to (interacted with) antigen. One of the features of the CAR of the invention is that it includes the CD3ζ intracellular domain as the intracellular domain. CD3 is a transmembrane polypeptide that associates with T cell receptor (TCR) and forms a TCR-CD3 complex. CD3 has γ, δ, ε and ζ chains as polypeptides, and forms a heterodimer or homodimer. The nucleotide sequences and amino acid sequences of all of the polypeptides are known. According to the invention, therefore, data relating to the nucleotide sequence of the CD3ζ intracellular domain can be obtained by searching for CD3 cDNA sequences using a commonly used nucleotide sequence database.

The CD3ζ intracellular domain may also include mutant sequences having the same function. Here, the term "mutant" means any mutant that includes a deletion, substitution or addition of one, several or more amino acids, the mutant preferably retaining the same function as the wild type.

The signal produced through a TCR complex alone is usually insufficient for activation of T cells, and a secondary signal (costimulatory signal) is often required. Natural T cell activation is transmitted by two different cytosolic signaling sequences, namely a sequence that initiates antigen-dependent primary activation via the TCR complex (primary cytosolic signaling sequence), and a sequence acting independently of the antigen and providing a secondary or costimulatory signal (secondary cytosolic signaling sequence). According to a preferred mode, the CAR of the invention includes a primary cytosolic signaling sequence and/or a secondary cytosolic signaling sequence as intracellular domains.

The primary cytosolic signaling sequence regulates primary activation of the TCR complex. A primary cytosolic signaling sequence that stimulates activation sometimes includes a signaling motif known as immunoreceptor tyrosine-based activation motif. (ITAM) (see Nature, 338, 383-384, 1989). A primary cytosolic signaling sequence that functions in an inhibitory manner, on the other hand, includes a signaling motif known as immunoreceptor tyrosine-based inhibitory motif (ITIM) (see J Immunol., 162, 897-902, 1999). According to the invention, an intracellular domain with ITAM, or ITIM depending on the case, may be used.

Intracellular domains with ITAM that may be used for the invention are not restricted, and include ITAM derived from CD3ζ, FcRγ, FcRβ, CD3γ, CD3δ, CD3ε, CD5, CD22, CD79a, CD79b and CD66d. Specifically, there may be mentioned peptides having the sequences comprising amino acid Nos. 51 to 164 of CD3ζ (NCBI RefSeq: NP 932170.1), amino acid Nos. 45 to 86 of FcεRIγ (NCBI RefSeq: NP 004097.1), amino acid Nos. 201 to 244 of FcεRIβ (NCBI RefSeq: NP 000130.1), amino acid Nos. 139 to 182 of CD3γ (NCBI RefSeq: NP 000064.1), amino acid Nos. 128 to 171 of CD3δ(NCBI RefSeq: NP 000723.1), amino acid Nos. 153 to 207 of CD3ε (NCBI RefSeq: NP 000724.1), amino acid Nos. 402 to 495 of CD5 (NCBI RefSeq: NP 055022.2), amino acid Nos. 707 to 847 of CD22 (NCBI RefSeq: NP 001762.2), amino acid Nos. 166 to 226 of CD79a (NCBI RefSeq: NP 001774.1), amino acid Nos. 182 to 229 of CD79b (NCBI RefSeq: NP 000617.1), and amino acid Nos. 177 to 252 of CD66d (NCBI RefSeq: NP 001806.2), as well as mutants thereof having the same function. These amino acid numbers, based on the NCBI RefSeq ID or GenBank amino acid sequence data listed in the present specification, are numbers assigned assuming the respective protein precursors (including the signal peptide sequence) as the full length. When the specific molecules mentioned above are used as the intracellular domain, the intracellular domain and/or transmembrane domain in the molecule can be appropriately utilized in the chimeric antigen receptor of the invention.

For this embodiment, the chimeric antigen receptor of the invention may include, in addition to the intracellular domain containing the primary cytosolic signaling sequence, also one or more identical or differing intracellular domains, containing a secondary cytosolic signaling sequence. There are no particular restrictions on intracellular domains containing secondary cytosolic signaling sequences that may be used for the invention, and they include sequences derived from CD2, CD4, CD5, CD8α, CD8β, CD28, CD134, CD137, ICOS and CD154. Specifically, there may be mentioned peptides having the sequences comprising amino acid Nos. 236 to 351 of CD2 (NCBI RefSeq: NP 001758.2), amino acid Nos. 421 to 458 of CD4 (NCBI RefSeq: NP 000607.1), amino acid Nos. 402 to 495 of CD5 (NCBI RefSeq: NP 055022.2), amino acid Nos. 207 to 235 of CD8α(NCBI RefSeq: NP 001759.3), amino acid Nos. 196 to 210 of CD8β(GenBank: AAA35664.1), amino acid Nos. 181 to 220 of CD28 (NCBI RefSeq: NP 006130.1), amino acid Nos. 214 to 255 of CD137 (4-1BB, NCBI RefSeq: NP 001552.2), amino acid Nos. 241 to 277 of CD134 (OX40, NCBI RefSeq: NP 003318.1) and amino acid Nos. 166 to 199 of ICOS (NCBI RefSeq: NP 036224.1), as well as mutants thereof having the same function. When the specific molecules mentioned above are used as the intracellular domain, the intracellular domain and/or transmembrane domain in the molecule can be appropriately utilized in the chimeric antigen receptor of the invention.

According to one specific embodiment, the chimeric antigen receptor (CAR) of the invention comprises, from the N-terminus to the C-terminus, (i) an extracellular domain containing the heavy chain variable region and light chain variable region (or the light chain variable region and heavy chain variable region) of anti-GPC-1 antibody, (ii) an intracellular domain, transmembrane domain and/or intracellular domain selected from among CD2, CD4, CD5, CD8α, CD8β, CD28, CD134, CD137, ICOS, CD154 and their combinations, and (iii) an intracellular domain selected from among CD3ζ, FcRγ, FcRβ, CD3γ, CD3δ, CD3ε, CD5, CD22, CD79a, CD79b and CD66d. According to a preferred embodiment, the CAR of the invention comprises, from the N-terminus to the C-terminus, (i) an extracellular domain comprising the heavy chain variable region (SEQ ID NO: 3) and light chain variable region (SEQ ID NO: 4) (or the light chain variable region and heavy chain variable region) of anti-GPC-1 antibody, (ii) the intracellular domain, transmembrane domain and intracellular domain of CD28, and (iii) the intracellular domain of CD3ζ (see Example 1). The heavy chain and light chain variable regions may also include mutants of these having the same function. Here, the term "mutant" means any mutant including a deletion, substitution or addition of one, several or more amino acids, the mutant preferably retaining the same function as the wild type.

CAR comprising multiple intracellular domains may have oligopeptide linkers or polypeptide linkers inserted between the intracellular domains to link them. The linkers used preferably have lengths composed of 2 to 10 amino acids. For example, a linker with a continuous Gly-Ser sequence may be used.

(2) Nucleic Acid Encoding Chimeric Antigen Receptor (CAR) of the Invention

According to the invention there is provided nucleic acid encoding the amino acid sequence of CAR according to (1) above. Unless otherwise specified, the term "nucleic acid (or nucleotide sequence) encoding an amino acid sequence" encompasses all nucleotide sequences that are mutually degenerate forms and code for the same amino acid sequence. So long as the nucleotide sequence encoding protein can include an intron in some form, the term "nucleotide sequence" encoding protein and RNA may also include introns.

The nucleic acid encoding the CAR can be easily created by a common method for specified CAR amino acid sequences. A nucleotide sequence encoding the amino acid sequence of each domain mentioned above can be obtained from the NCBI RefSeq ID or GenBank Accession No. for the amino acid sequence, and nucleic acid of the invention can be prepared using a standard molecular biological and/or chemical procedure. For example, nucleic acid can be synthesized based on the nucleotide sequences, or DNA fragments obtained from a cDNA library using Polymerase Chain Reaction (PCR) may be combined to create the nucleic acid of the invention. According to a particular mode, the nucleic acid encoding the extracellular domain to be used in the nucleic acid of the invention is preferably a nucleotide sequence encoding the heavy chain variable region of anti-GPC-1 antibody (SEQ ID NO: 1) and a nucleotide sequence encoding the light chain variable region (SEQ ID NO: 2). The nucleotide sequences encoding the heavy chain and light chain variable regions may also be substantially homologous nucleotide sequences having the same function. The term "substantially homologous" includes two or more biological molecular sequences that are significantly analogous on the primary structural nucleotide sequence level. For example, "substantially homologous", in the context of two or more nucleic acid sequences, means at least about 75% identity, preferably at least about 80% identity, more preferably at least about 85% identity or at least about 90% identity, and yet more preferably at least about 95% identity, even yet more preferably at least about 97% identity, still yet more preferably at least about 98% identity, and most preferably at least about 99% identity.

The nucleic acid of the invention may be linked with another nucleic acid so as to be expressed under the control of a suitable promoter. The promoter used may be one that promotes constitutive expression, or one induced by a drug or the like (for example, tetracycline or doxorubicin). In order to achieve efficient transcription of the nucleic acid, it may be linked with nucleic acid containing other regulating elements such as an enhancer sequence or terminator sequence that function in combination with the promoter or transcription initiation site. In addition to the nucleic acid of the invention, a gene that can serve as a marker for confirmation of expression of the nucleic acid (for example, a drug resistance gene, a gene coding for a reporter enzyme, or a gene coding for a fluorescent protein) may also be used in appropriate combinations. An example of a suitable promoter is the immediate-early cytomegalovirus (CMV) promoter sequence. This promoter sequence is a powerful constitutive promoter sequence that can drive high-level expression of a desired polynucleotide sequence that is functionally linked to it. The term "functionally linked" as used here refers to functional linkage between a regulatory sequence and a heterogenous nucleic acid sequence that results in expression of the latter. For example, when a first nucleic acid sequence is situated in a functional relationship with a second nucleic acid sequence, the first nucleic acid sequence is said to be functionally linked with the second nucleic acid sequence. For example, if a promoter affects transcription or expression of a coding sequence, the promoter is "functionally linked" with the coding sequence. Functionally linked DNA sequences are usually contiguous, and are in the same reading frame when it is necessary to join two protein coding regions.

Other examples of suitable promoters that may be used include Elongation Factor-1α (EF-1α), simian virus 40 (SV40) early promoter, mouse mammary tumor virus (MMTV), human immunodeficiency virus (HIV) long terminal repeat (LTR) promoter, MoMuLV promoter, avian leukemia virus promoter, Epstein-Barr virus immediate early promoter, Raus sarcoma virus promoter, and human gene promoters including, but not limited to, actin promoter, myosin promoter, hemoglobin promoter and creatine kinase promoter, although there is no limitation to these, and other constitutive promoter sequences may be used. Moreover, the present invention is not restricted to the use of constitutive promoters. Inducible promoters are also implied as components of the present invention. The use of an inducible promoter provides a molecular switch that can switch on expression of a polynucleotide sequence to which it is functionally linked, when such expression is desired, or switch it off when such expression is not desired. Examples of inducible promoters include, but are not limited to, metallothionein promoter, glucocorticoid promoter, progesterone promoter and tetracycline promoter.

(3) Method for Producing Cells Expressing Chimeric Antigen Receptor (CAR) of the Invention The method for producing cells expressing the CAR of the invention comprises a step of transferring nucleic acid encoding CAR according to (2) above into cells. The step is carried out ex vivo. For example, it can be produced by transformation of cells ex vivo utilizing a virus vector or a non-virus vector that includes the nucleic acid of the invention.

The method of the invention may employ cells from a mammal, such as human-derived cells or cells derived from a non-human mammal such as a monkey, mouse, rat, pig, cow or dog. The cells to be used in the method of the invention are not particularly restricted, and any desired cells may be used. For example, cells harvested, isolated, purified and induced from body fluid, tissue or organs, such as blood (peripheral blood or umbilical cord blood) or bone marrow may be used. Peripheral blood mononuclear cells (PBMC), immunocytes (for example, dendritic cells, B cells, hematopoietic stem cells, macrophages, monocytes, NK cell or hematocytes (neutrophils or basophils)), umbilical cord blood mononuclear cells, fibroblasts, adipocyte precursors, hepatocytes, skin keratinocytes, mesenchymal stem cells, adipose stem cells, various cancer cell lines and neural stem cells may be used. According to the invention it is preferred to use T cells, T cell precursors (hematopoietic stem cells, lymphocyte precursors and the like) or cell populations containing them. T cells include $CD8^+$ T cells, $CD4^+$ T cells, regulatory T cells, cytotoxic T cells and tumor-infiltrating lymphocytes. Cell populations containing T cells and/or T cell precursors include PBMC. The cells may be ones harvested from the body, or further subjected to amplifying culturing, or ones established as cell lines. When it is desirable to transplant the produced CAR-expressing cells or cells differentiated to such cells into the body, it is preferred to transfer the nucleic acid into cells harvested from the body itself or a body of the same species.

According to the invention, nucleic acid encoding the CAR of the invention may be inserted into a vector and the vector introduced into cells. For example, retrovirus vectors (including oncoretrovirus vectors, lentivirus vectors and pseudotyped vectors) or virus vectors such as adenovirus vectors, adeno associated virus (AAV) vector, simian virus vector, vaccinia virus vector or Sendai virus vector, Epstein-Barr virus (EBV) vector and HSV vector, may be used. Preferred virus vectors are those incapable of replication so that they cannot auto-replicate in the infected cells.

Non-virus vectors may also be used for the invention, in combination with liposomes, or condensation agents such as the cationic lipids described in WO96/10038, WO97/18185, WO97/25329, WO97/30170 and WO97/31934. The nucleic acid of the invention can be introduced into the cells by calcium phosphate transfection, lipofection, DEAE-dextran, electroporation or particle bombardment.

When a retrovirus vector is used, for example, appropriate packaging cells may be selected based on the LTR sequence and packaging signal sequence of the vector, and the cells used to prepare retrovirus particles. Examples of packaging cells include PG13 (ATCC CRL-10686), PA317 (ATCC CRL-9078), GP+E-86 or GP+envAm-12 (U.S. Pat. No. 5,278,056), and Psi-Crip (Proc. Natl. Acad. Sci. USA, Vol. 85, p. 6460-6464(1988)). In addition, retrovirus particles can be formed using 293 cells or 293T cells that have high transfection efficiency. Retrovirus vectors produced based on numerous types of retroviruses, and packaging cells that can be used for packaging of the vectors, are widely available from various manufacturers.

A functional substance that increases transfer efficiency may be used in the step of transferring the nucleic acid into cells (WO95/26200 and WO00/01836, for example). Substances that increase transfer efficiency include substances with activity of binding to virus vectors, such as fibronectin and fibronectin fragments. It is preferred to use a fibronectin fragment with a heparin-binding site, such as the fragment marketed as RetroNectin CH-296 (Takara Bio, Inc.). Another substance that may be used is polybrene, as a synthetic polycation having the effect of increasing infection efficiency of the retrovirus into cells, or fibroblast growth factor, type V collagen, polylysine or DEAE-dextran.

(4) Cells Expressing Chimeric Antigen Receptor (CAR) of the Invention

The cells expressing the CAR of the invention are cells in which nucleic acid encoding the CAR of (2) above has been transferred and expressed by the production method of (3) above.

The cells of the invention are activated upon transfer of the signal into the cells in response to binding with a specific antigen through CAR. Activation of the CAR-expressing cells will differ depending on the type of host cells and/or the intracellular domain of the CAR, and for example, release of cytokines, augmentation of cell proliferation or cell surface molecule modification may be used as an index for confirmation. For example, release of a cytotoxic cytokine (tumor necrosis factor, lymphotoxin or the like) from the activated cells causes disruption of the target cells expressing the antigen (specifically, squamous cell carcinoma cells). In addition, other immunocytes such as B cells dendritic cells, NK cells or macrophages are stimulated by cytokine release or cell surface molecule modification.

(5) Cell Preparation and Medical Composition of the Invention, and Method of Treatment and Prevention Using them According to the invention, cells expressing the chimeric antigen receptor (CAR) can be used for treatment and/or prevention of a disease, and typically a cell preparation and medical composition may can be provided. The term "treatment" as used here includes mitigation (alleviation) of characteristic symptoms or accessory symptoms of a target disease, and arrest or retardation of aggravation of symptoms, and treatment also includes improvement in the disease. The term "prevention" means halting or delaying onset or expression of a disease (disorder) or its symptoms, or reducing the risk of its onset or expression. According to one mode, the cell preparation of the invention may comprise CAR-expressing cells of the invention as an active ingredient, together with an appropriate excipient. According to another mode, the medical composition of the invention comprises nucleic acid, CAR, vector and/or cells of the invention in an effective amount as an active ingredient, together with an appropriate medically acceptable excipient. The excipient to be included in the cell preparation and medical composition may be any of various cell culture media, phosphate-buffered saline, isotonic brine, or the like. The diseases which may be targets of treatment by CAR-expressing cells include solid tumors specifically expressing GPC-1, and more specifically pancreatic carcinoma, breast cancer, brain tumors and various squamous cell carcinomas. The squamous cell carcinomas are not particularly restricted and include esophageal cancer, lung cancer and cervical cancer. The individual with a disease to be treated is not particularly restricted, and may be a mammal such as a primate, human, dog, cat, cow, horse, pig or sheep, but it is preferably a human. For treatment of the disease, a therapeutically effective amount of the cell preparation of the invention is administered to a patient. The term "effective amount" as used in the present specification means an amount that provides a therapeutic or prophylactic advantage. The route of administration is not restricted, as is recognized by those skilled in the art, and may be parenteral administration, such as intracutaneous, intramuscular, subcutaneous, intraperitoneal, intranasal, intraarterial, intravenous, intratumoral or afferent vessel administration, by injection or infusion.

The following examples serve as illustration of different modes of the present disclosure. It will be apparent to a person skilled in the art that various modifications may be made to both the materials and methods while still being within the scope of the present disclosure. All of the reagents and solvents purchased from commercial product suppliers were used without further purification or processing.

EXAMPLES

Example 1: Construction of Anti-GPC-1-CAR Gene-Carrying Virus Vector

The nucleotide sequences coding for the heavy chain variable region (VH) and light chain variable region of anti-GPC-1 antibody were identified from nucleotide sequence data for the heavy chain and light chain portions of monoclonal anti-GPC-1 antibody (WO2015/098112), that were prepared from chicken at the National Institutes of Biomedical Innovation, Health and Nutrition, one of the applicants. Kozak sequence-LS (leader sequence)-VL-linker-VH sequence (Type A) or -LS-VH-linker-VL sequence (Type B) double-stranded DNA was synthesized and cloned in a CAR expression vector (pMS3-F) (FIG. 1). The recombinant retrovirus vector was transfected into G3T-hi cells together with pGP vector and pE-Eco vector, to prepare a retrovirus vector solution for infection. PG13 cells (GaLV env.) were infected with the solution to create producer cells. An anti-GPC-1-CAR gene-carrying retrovirus vector solution (two types, Type A and Type B) were prepared from the cells.

Example 2: Preparation of Anti-GPC-1-CAR-T Cells

Blood was collected from a human and the peripheral blood mononuclear cells (PBMC) were separated using Lymphoprep (#1114544 by Axis-Shield). The separated PBMCs were added to AIM-V (Life Technologies #087-0112DK)+10% human AB serum (Gemini #100-512) to a cell concentration of $2 \times 10^6/2$ ml/well. Human rIL2 (500 IU/ml) and anti-human CD3 antibody (OKT-3) (50 ng/ml) were added, and after seeding in a 24-well plate, culturing was carried out at 37° C., 5% $CO_2$ for 2 days. On the following day, 10 μL RetroNectin (#T100B by Takara Bio, Inc.) (1 mg/ml)+400 uL BS was added to each well of a separate non-treated 24-well plate (BD #351147), and the plate was allowed to stand overnight at 4° C. On the following day, the RetroNectin-coated plate was rinsed with 1 ml of PBS, and then developed with 3% BSA/PBS at 500 uL/well and allowed to stand for 30 minutes at room temperature, and then rinsed with 1 ml of PBS. The retrovirus vector solution (Type A or Type B) carrying the anti-GPC-1-CAR gene prepared in Example 1 was diluted 2- to 5-fold, and added to the RetroNectin-coated plate at 1 ml/well. The plate was centrifuged at 3044 rpm, 32° C. for 2 hours to adsorb the virus on the RetroNectin at the bottom of the plate. After centrifugation, the virus solution was removed, the PBMCs that had been previously cultured for 2 days were added at $5 \times 10^5/500$ μL (AIM-V+10% human AB serum)/well, and human rIL2 (500 IU/ml) was added. After centrifugation at 2153 rpm for 10 minutes, culturing was initiated at 37° C., 5% $CO_2$. On the following day, 1.5 ml of AIM-V+10% human AB serum and human rIL2 (500 IU/ml) were added. The number of wells was doubled thereafter each time the cells reached confluency.

Example 3: IFN-γ Production Test

Figure 2:
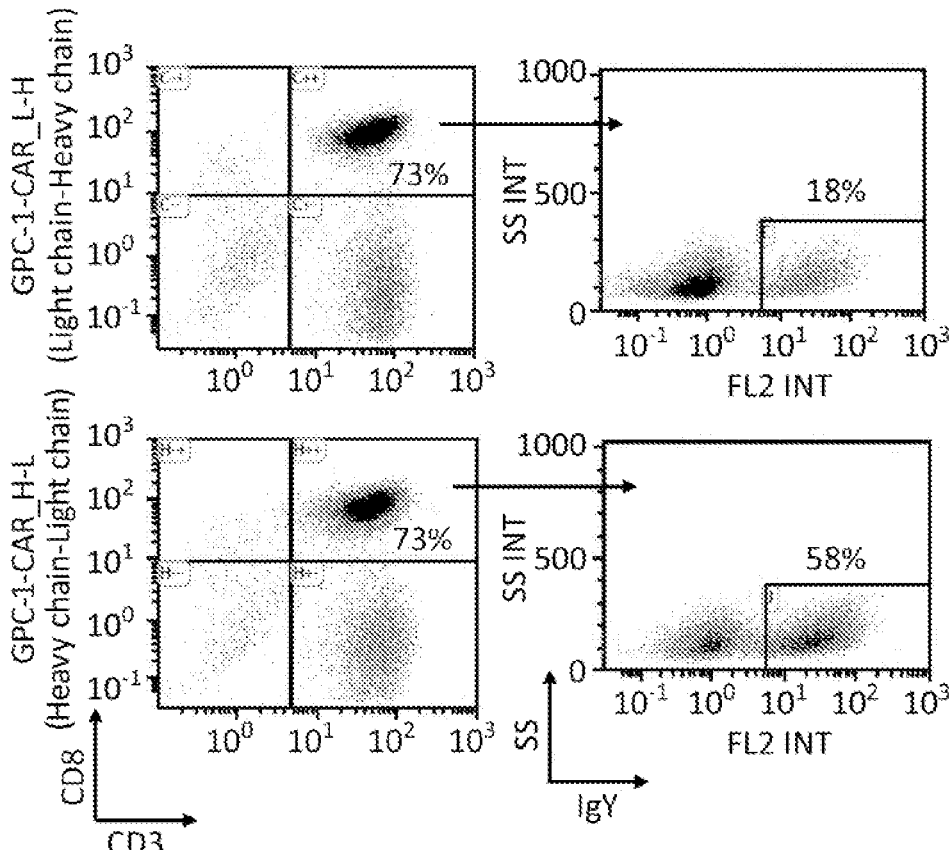
FIG. 2 shows expression of an immunogen receptor (GPC-1-CAR) in created GPC-1-CAR-T cells.
Figure 3:
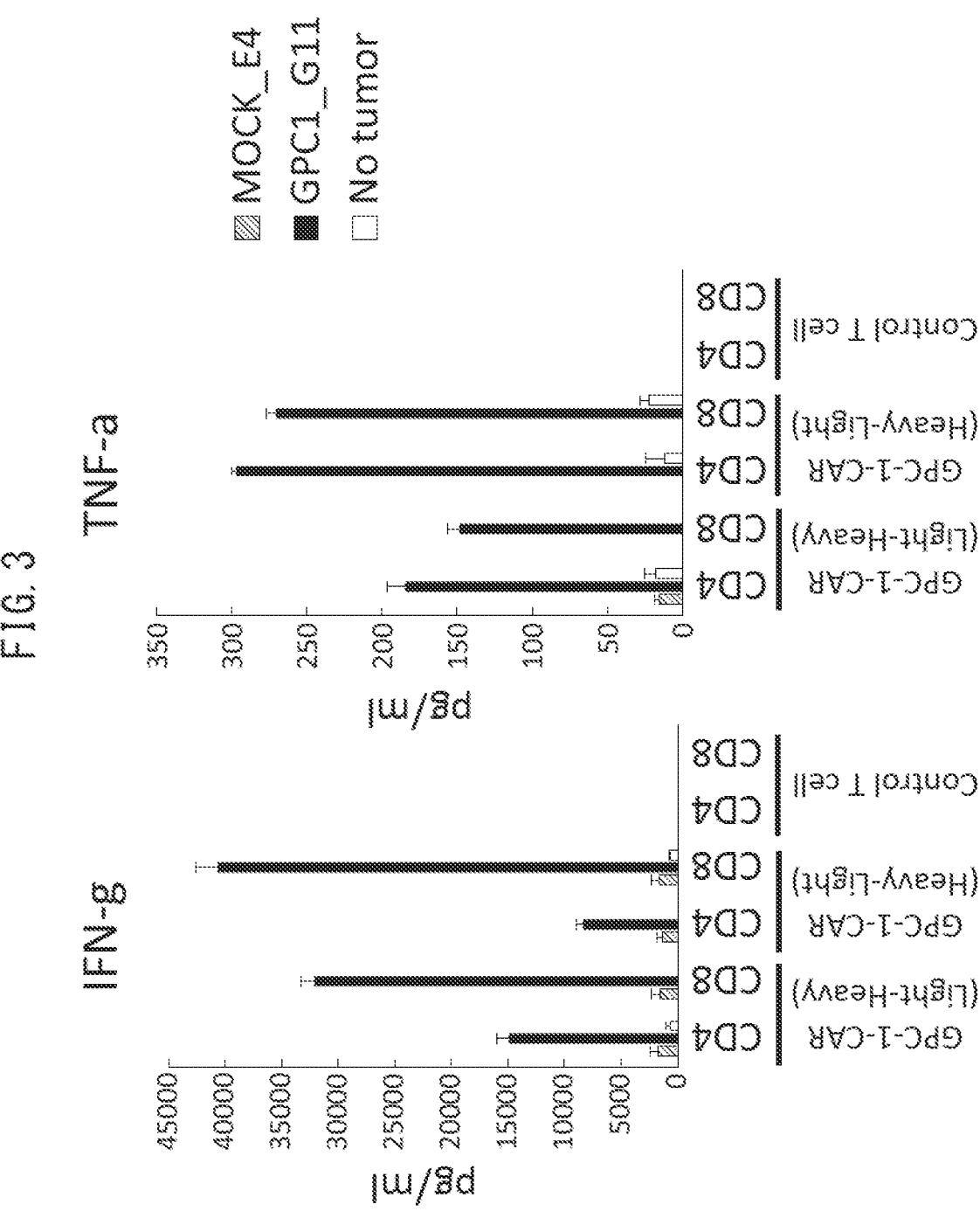
FIG. 3 shows GPC-1-specific IFN-γ and TNF-α production by immunogen receptor-expressing T cells.
Figure 4:
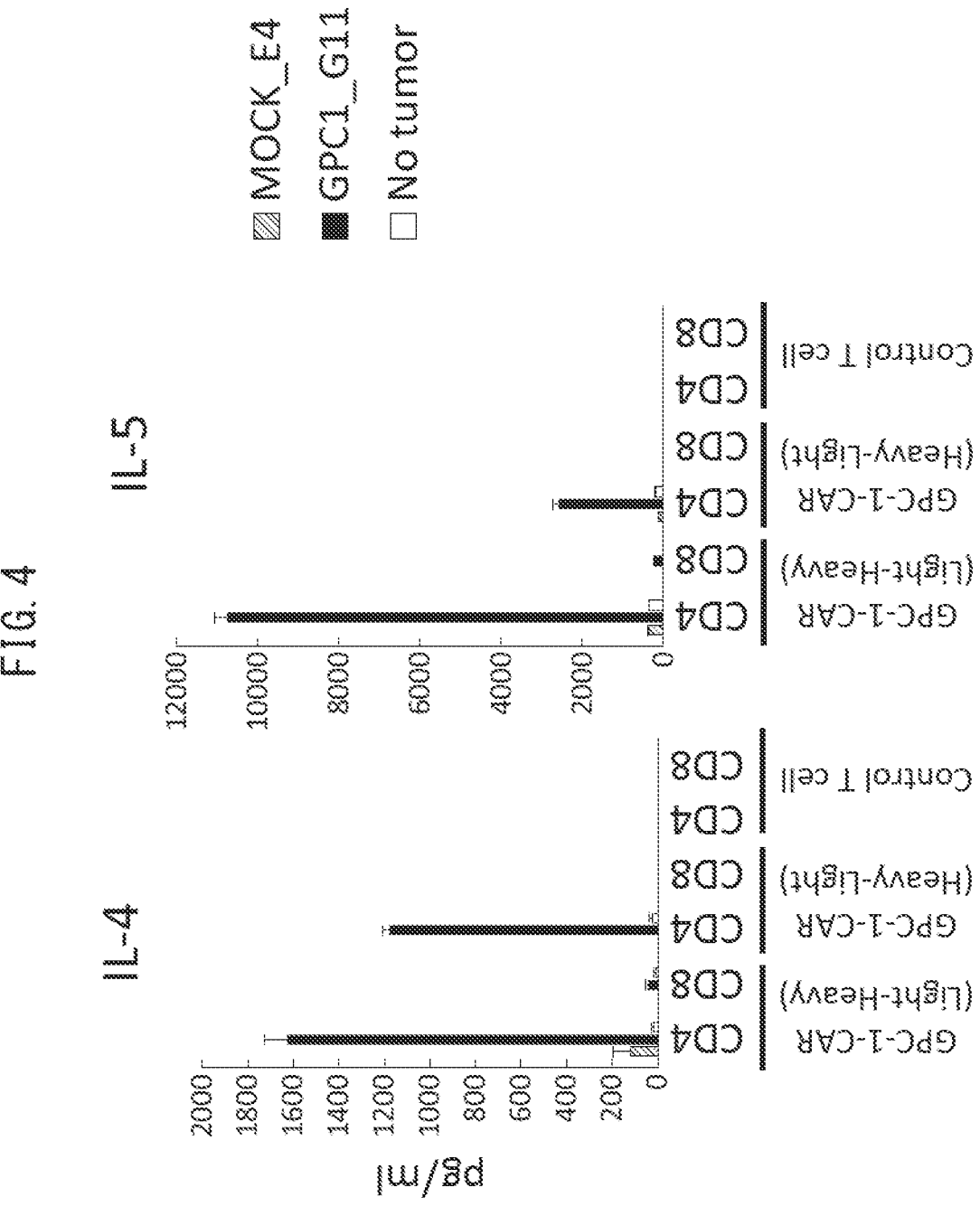
FIG. 4 shows GPC-1-specific IL4 and IL5 production by immunogen receptor-expressing T cells.

Human activated peripheral blood mononuclear cells were infected with the GPC-1-CAR gene-carrying retrovirus vector (Type A or Type B), and then anti-human CD8 antibody, anti-human CD4 antibody or anti-chicken IgY antibody was used for staining to confirm expression of GPC-1-CAR (FIG. 2). A cell sorter was then used to separate the CD8-positive anti-GPC-1-CAR-T cells and CD4-positive anti-GPC-1-CAR-T cells. The T cells ($1$-$2 \times 10^5$ cells) and a GPC-1 forced expression cell line (LK-GPC1(G11)) or a GPC-1 non-expressing cell line (LK-MOCK) ($1 \times 10^5$ cells) were suspended in 200 μl of AIM-V+10% human AB serum and seeded in a 96-well plate. After 24 hours, the culture supernatant was collected and the IFN-γ, TNF-α, IL-4 and IL-5 concentrations were measured by ELISA. Production of IFN-γ, TNF-α, IL-4 and IL-5 by the genetically modified T cells was measured as a high level of GPC-1-specific expression (see FIG. 3 and FIG. 4).

Example 4: Cytotoxicity Test

Figure 5:
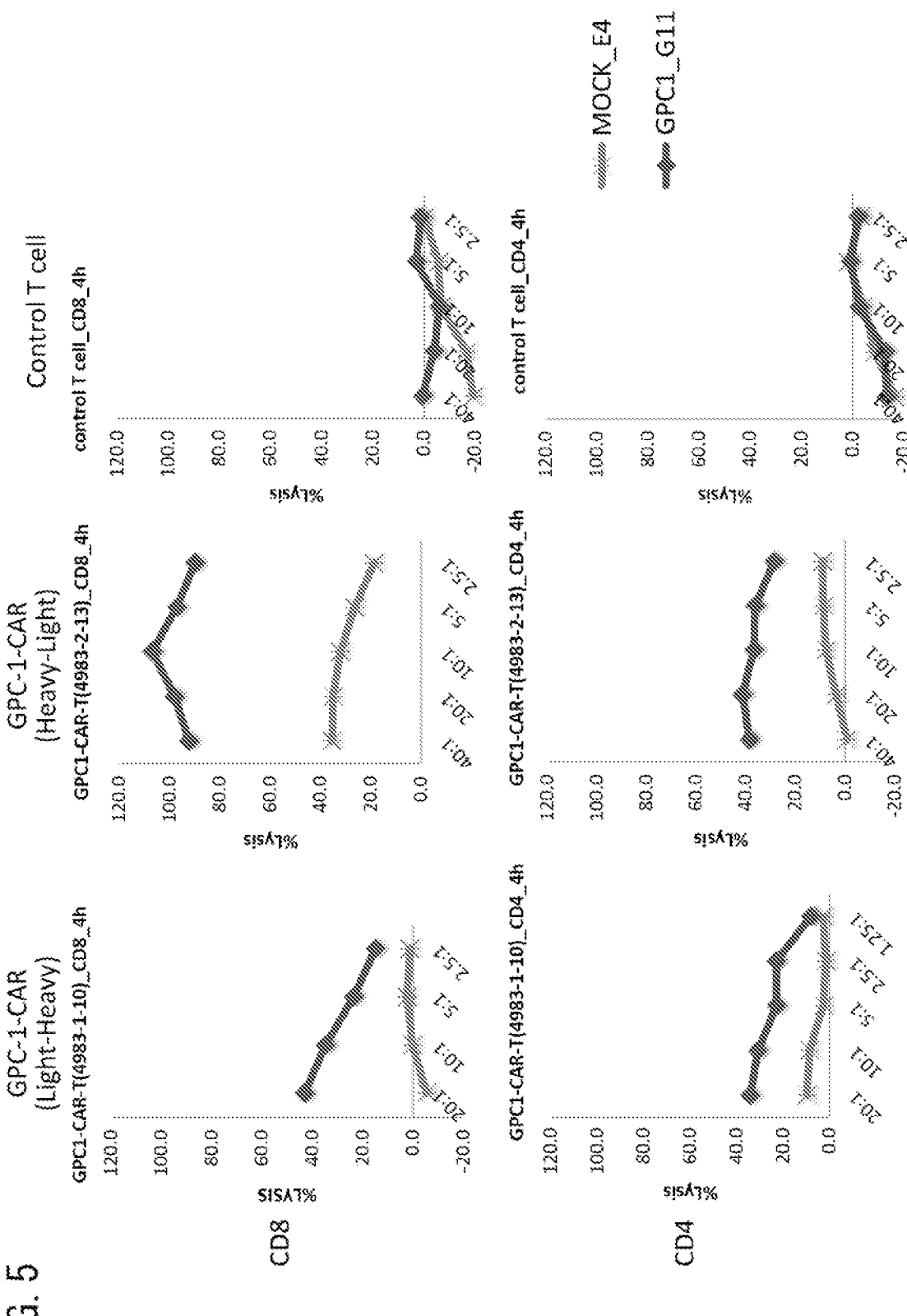
FIG. 5 shows GPC-1-specific cytolysis by immunogen receptor-expressing T cells.

After labeling a GPC-1 forced expression cell line (LK-GPC1(G11)) or a GPC-1 non-expressing cell line (LK-MOCK) with Calcein-AM, as the target cells, $5 \times 10^3$ cells were seeded in a 96-well plate. CD8-positive anti-GPC-1-CAR-T cells or CD4-positive anti-GPC-1-CAR-T cells were added as effector cells in 40-fold, 20-fold, 10-fold, 5-fold and 2.5-fold amounts, and after 4 hours of culturing, the Calcein-AM in the supernatant was measured with a fluo-rophotometer and the proportion of cells injured by the T cells was calculated. The anti-GPC-1-CAR-T cells lysed the GPC-1-specific cells at a very high rate compared to the Mock (FIG. 5).

Figure 6:
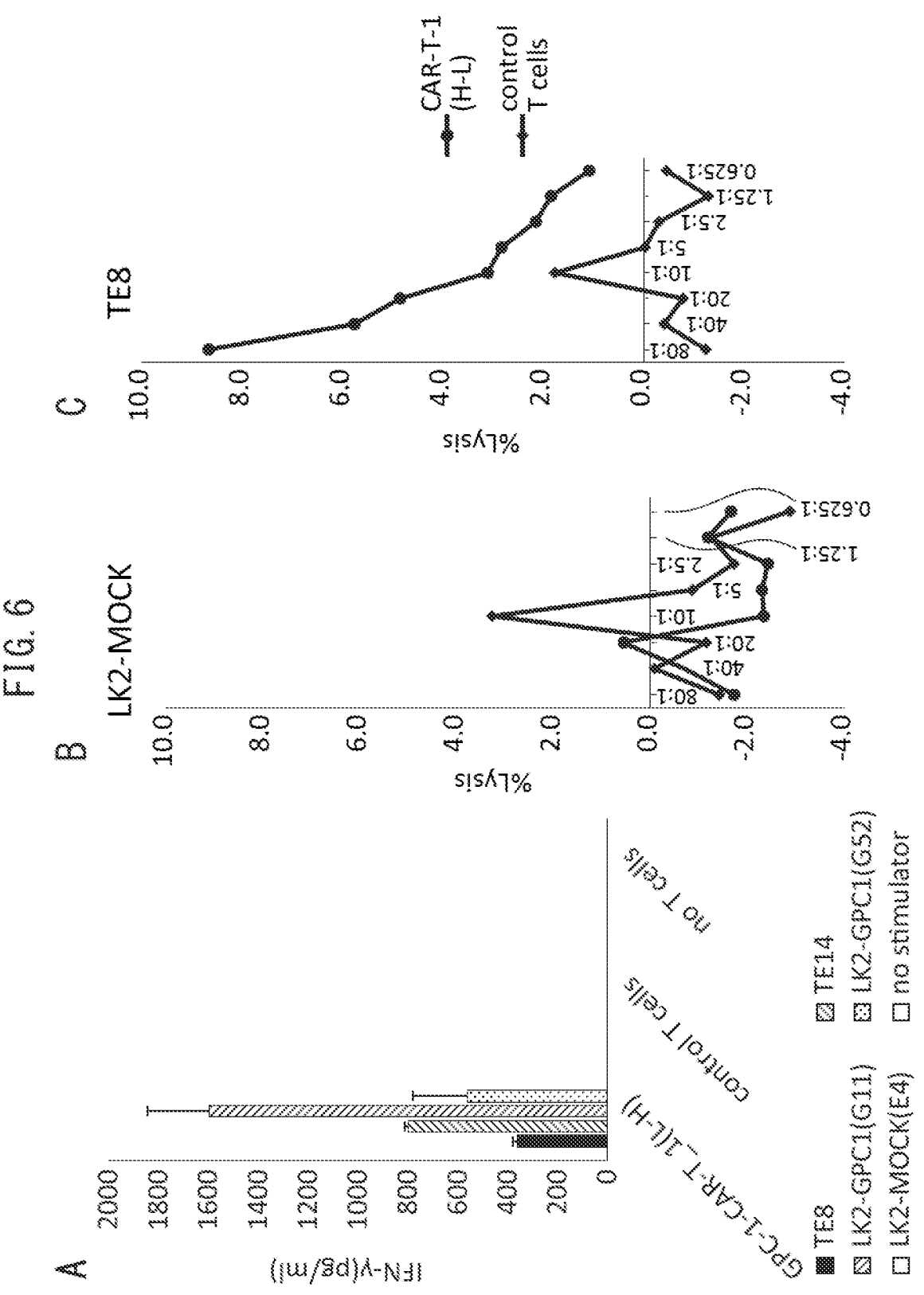
FIG. 6 shows GPC-1-specific IFN-γ production by immunogen receptor-expressing T cells, and GPC-1-specific cytolysis by the T cells.

Example 5: Recognition of Esophageal Cancer Cells and Toxicity Effect by Anti-GPC-1-CAR-T Cells The test methods described in Examples 3 and 4, were used to examine recognition of and toxicity effect on GPC-1-expressing esophageal cancer cell lines ("TE8" and "TE14") by anti-GPC-1-CAR-T cells. As test examples in addition to the esophageal cancer cell line, there were used a GPC-1 forced expression cell line ("LK2-GPC1(G11)" and "LK2-GPC1(G52)"), a GPC-1-non-expressing cell line ("LK-MOCK (E4)") and a system without addition of anti-GPC-1-CAR-T cells ("no stimulator"). As shown in FIG. 6A, the anti-GPC-1-CAR-T cells produced IFN-γ in response to the GPC-1-expressing cells ("TE8", "TE14", "LK2-GPC1(G11)" and "LK-GPC1(G52)"). On the other hand, IFN-γ production by the anti-GPC-1-CAR-T cells was not observed with "LK2-MOCK (E4)" and "no stimulator" that were used as negative controls. Likewise, no IFN-γ production was observed with control T cells and "no T cells" (no stimulation by T cells), which where not anti-GPC-1-CAR-T cells. This demonstrates that induction of IFN-γ production by anti-GPC-1-CAR-T cells is GPC-1-specific.

A cytotoxicity test was conducted by the same method as Example 4, using "TE8" and "LK2-MOCK" as the test cells. With GPC-1-expressing TE8, the cytolysis rate of TE8 increased as the proportion of anti-GPC-1-CAR-T cells added increased, and therefore the anti-GPC-1-CAR-T cells lysed the cells in a GPC-1-specific manner (FIG. 6B). No cytolysis was observed when the "control T cells" were used as the added cells with the GPC-1-non-expressing cell line ("LK-MOCK)" (FIG. 6C).

Example 6: Treatment Model with Human Esophageal Cancer Cell Line

Figure 7:
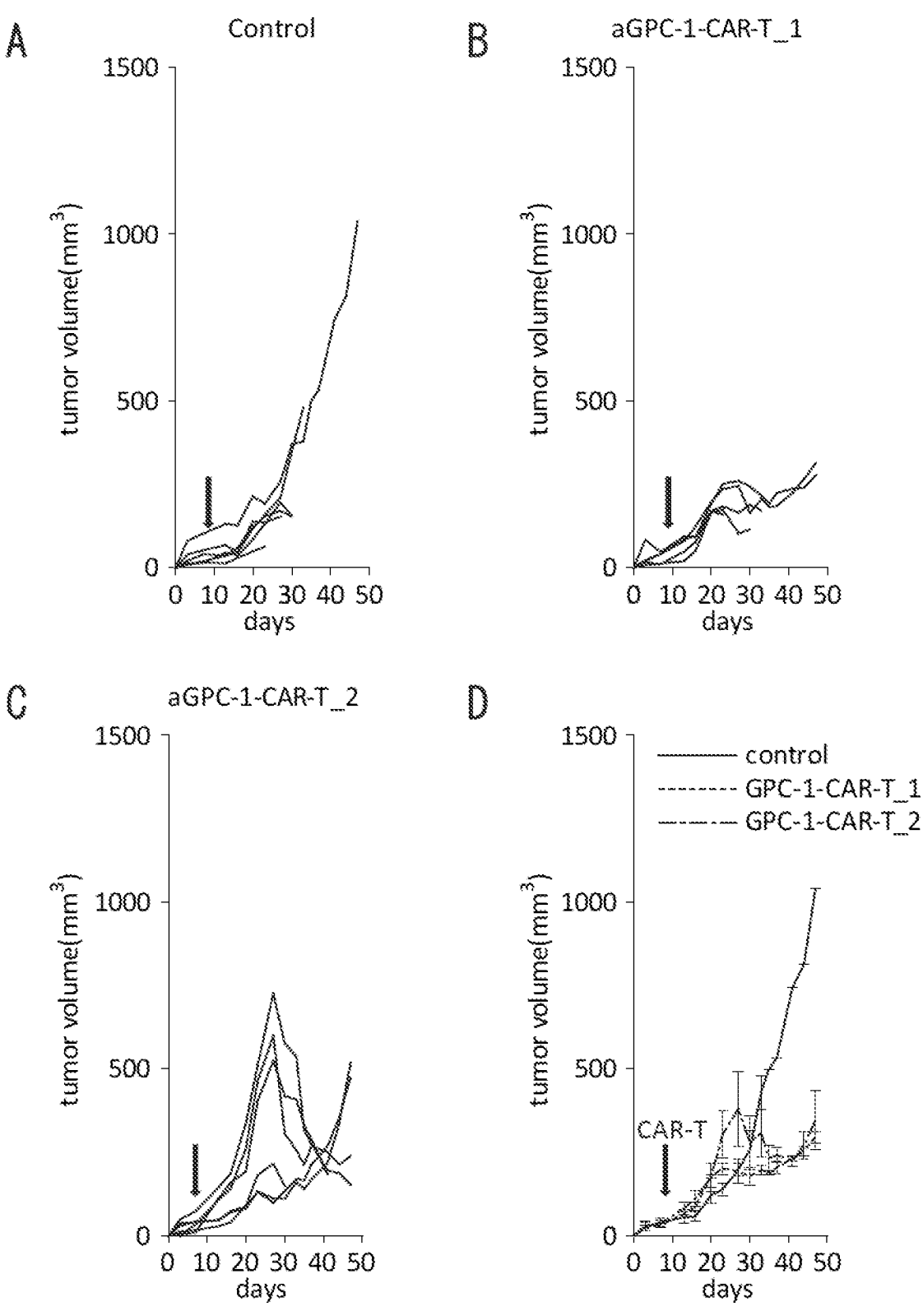
FIG. 7 shows in vivo suppression of tumor cell increase in mice with a transplanted human esophageal cancer cell line (TE14), by immunogen receptor-expressing T cells.

The human esophageal cancer cell line TE14 ($3 \times 10^6$ cells) was subcutaneously transplanted into NOG (NOD.Cg-Prkdcscid Il2rgtm1Sug/Jic) mice (groups). After 9 days (with confirmation that the TE14 graft had taken), anti-GPC-1-CAR-T cells or activated T cells without CAR gene transfer (negative control group) were intraperitoneally administered at $2.5 \times 10^7$ cells each. The tumor volume (mm$^3$) in each mouse was periodically measured, calculat-ing the long diameter×short diameter×short diameter/2 value, and the results are shown FIG. 7. The negative control group was a system administered non-CAR-gene-trans-ferred activated T cells, and the tumor volume was shown to increase with time (FIG. 7A). On the other hand, in a system administered anti-GPC-1-CAR-T cells, where "aGPC-1-CAR-T_1" and "aGPC-1-CAR-T_2" respectively corre-spond to "GPC-1-CAR L_H" and "GPC-1-CAR H_L" shown in FIG. 2, it is seen that increase in tumor volume was suppressed when using these cells (FIGS. 7A and 7B). FIG. 7D shows the change in tumor volume of each as the mean±SD. In all of the systems with addition of anti-GPC-1-CAR-T cells, marked suppression of tumor volume increase is seen compared to the negative control group.

Figure 8:
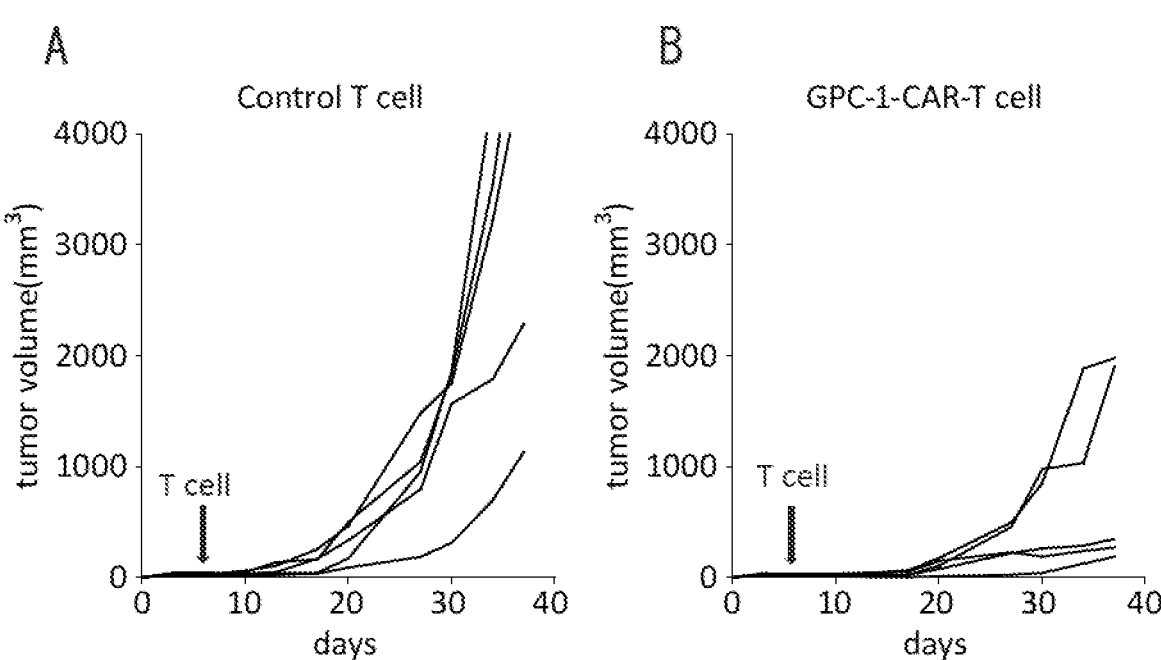
FIG. 8 shows in vivo suppression of tumor cell increase in mice transplanted with a forced GPC-1 expression mouse colon cancer cell line (MC38), by immunogen receptor-expressing T cells.
Figure 8:
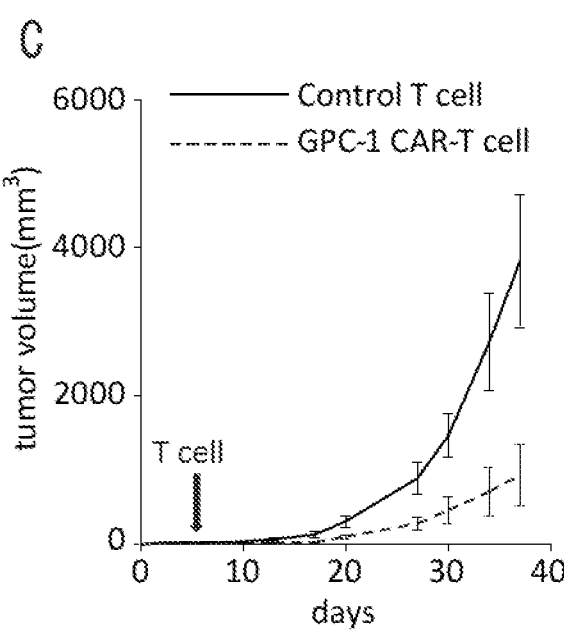

Example 7: Treatment Model with GPC-1 Forced Expression Mouse Colon Cancer Cell Line Since the GPC-1 CAR gene of the invention can recog-nize both human and mouse GPC-1, mouse cells were used for the subsequent treatment experiments. Gene transfer of mouse GPC-1 into the mouse colon cancer cell line MC38 was carried out using lentivirus vector, to create a forced expression line (MC38-GPC-1). The plasmid shown in FIG. 1 was used to create an ecotropic retrovirus vector for the GPC-1-CAR gene, and mouse GPC-1-CAR-T cells were prepared. Specifically, first mouse spleen cells ($2 \times 10^6$) were cultured for 24 hours in complete RPMI 1640 medium (RPMI 1640 basal medium with addition of 10% FCS, 10 mM HEPES, 1 mM sodium pyruvate, 1% MEM NEAA (Non-essential amino acids) (#11140-050 by Gibco), 2 mM L-glutamine, 0.05 mM 2-mercaptoethanol, as final concen-trations) containing ConA (2 μg/ml), mouse IL-7 (1 ng/ml) and human IL-2 (500 IU/ml), to prepare activated mouse T cells. Next, the retrovirus was used to transfer the GPC-1-CAR gene ("GPC-1-CAR L_H" of FIG. 2) into the activated mouse T cells, to create GPC-1-CAR-T cells. The transfer method was according to the procedure described in Example 2. However, the number of activated mouse T cells added to each well of the RetroNectin-coated plate was $2 \times 10^6$. After infection, the cells were cultured in complete RPMI 1640 medium containing human IL-2 (500 IU/mL), anti-mouse CD3 antibody (1 μg/mL) and anti-mouse CD28 antibody (1 μg/mL), and the same procedure was carried out again on the following day. Next, the prepared CAR-T cells were cultured in complete RPMI 1640 medium containing human IL-2 (500 IU/mL), and cultured for 5-7 days while doubling the number of wells each time the cells reach confluency. The transfer efficiency of the GPC-1-CAR gene was approximately 20%. Next, $5 \times 10^5$ MC38-GPC-1 cells were subcutaneously transplanted into C57BL/6 mice, which were exposed to 5 Gy of radiation after 3 days (after confirming that the graft had taken). The previously pre-pared GPC-1-CAR-T cells ($2 \times 10^7$) were then intraperitone-ally administered. Beginning on the same day, IL2 was intraperitoneally administered twice a day for 3 consecutive days (50,000 IU/mouse/dose). Non-CAR-gene-transferred activated T cells were administered to the negative control group. The tumor volume (mm$^3$) in each mouse was mea-sured, calculating the long diameter×short diameter×short diameter/2 value. The results of periodically recording the change in tumor volume in each group are shown in FIG. 8. FIGS. 8A and 8B show changes in tumor volume for each mouse individual in the negative control group and GPC-1-CAR-T cell-administered group, and FIG. 8C shows the change in tumor volume for each group as the mean±SD. As clearly seen from the results in FIG. 8C, the tumor volume increase was markedly suppressed in the mice administered the GPC-1-CAR-T cells, compared to the control group.

Moreover, there were absolutely no side-effects in the normal mice, and an antitumor effect was observed only in the cancer animal model. Incidentally, because these models are in vivo models with normally functioning immune systems, it may be assumed that they adequately render the clinical setting for humans. This type of experimental system cannot be constructed with other CRT-T cells.

INDUSTRIAL APPLICABILITY

The chimeric antigen receptor of the invention and genetically modified cells expressing them are useful for treatment and/or prevention of solid tumors such as squamous cell carcinoma, without side-effects.

It is to be noted that other alternative methods exist for carrying out the embodiments disclosed in the present specification. Therefore, the embodiments are merely for illustrative purposes and should not be considered to be restrictive. Moreover, the claims are not restricted by the detailed description provided in the present specification, and the right of patent applies to the entirety of their scope and equivalent subject matter.

The invention claimed is:

1. A method for treatment and/or prevention of a solid tumor expressing GPC-1, comprising administering a CAR-T cell comprising a nucleic acid to an individual in need thereof, wherein the nucleic acid comprises an extracellular domain capable of binding to glypican-1 (GPC-1), a transmembrane domain and one or more intracellular domains, wherein at least one of the intracellular domains is an intracellular domain comprising a primary cytosolic signaling sequence; wherein the extracellular domain capable of binding to GPC-1 comprises the heavy chain variable region (VH) and light chain variable region (VL) of anti-GPC-1 antibody and wherein the nucleotide sequence encoding the heavy chain variable region of anti-GPC-1 antibody comprises the nucleotide sequence listed as SEQ ID NO: I or a nucleotide sequence with at least 95% identity therewith and having the same function, and the nucleotide sequence encoding the light chain variable region comprises the nucleotide sequence listed as SEQ ID NO: 2 or a nucleotide sequence with at least 95% identity therewith and having the same function.

2. The method according to claim 1, wherein the solid tumor is squamous cell carcinoma, esophageal cancer or colon cancer.

3. A vector containing a nucleic acid, wherein the nucleic acid comprises an extracellular domain capable of binding to glypican-1 (GPC-1), a transmembrane domain and one or more intracellular domains, wherein at least one of the intracellular domains is an intracellular domain comprising a primary cytosolic signaling sequence; wherein the extracellular domain capable of binding to GPC-1 comprises the heavy chain variable region (VH) and light chain variable region (VL) of anti-GPC-1 antibody and wherein the nucleotide sequence encoding the heavy chain variable region of anti-GPC-1 antibody comprises the nucleotide sequence listed as SEQ ID NO: I or a nucleotide sequence with at least 95% identity therewith and having the same function, and the nucleotide sequence encoding the light chain variable region comprises the nucleotide sequence listed as SEQ ID NO: 2 or a nucleotide sequence with at least 95% identity therewith and having the same function.

4. Cells comprising the vector of claim 3, wherein the cells express a chimeric antigen receptor.

5. The cells according to claim 4, wherein the cells are T cells or a cell population comprising T cells.

6. A cell preparation containing cells according to claim 5, for treatment of a solid tumor expressing GPC-1.

7. The cell preparation according to claim 6, wherein the solid tumor is squamous cell carcinoma, esophageal cancer or colon cancer.

8. A medical composition comprising a nucleic acid and a medically acceptable excipient, wherein the nucleic acid comprises an extracellular domain capable of binding to glypican-1 (GPC-1), a transmembrane domain and one or more intracellular domains, wherein at least one of the intracellular domains is an intracellular domain comprising a primary cytosolic signaling sequence; wherein the extracellular domain capable of binding to GPC-1 comprises the heavy chain variable region (VH) and light chain variable region (VL) of anti-GPC-1 antibody and wherein the nucleotide sequence encoding the heavy chain variable region of anti-GPC-1 antibody comprises the nucleotide sequence listed as SEQ ID NO: I or a nucleotide sequence with at least 95% identity therewith and having the same function, and the nucleotide sequence encoding the light chain variable region comprises the nucleotide sequence listed as SEQ ID NO: 2 or a nucleotide sequence with at least 95% identity therewith and having the same function.

9. A medical composition according to claim 8, for treatment of a solid tumor expressing GPC-1.

10. A medical composition according to claim 9, wherein the solid tumor is squamous cell carcinoma, esophageal cancer or colon cancer.

11. A method for treatment of a solid tumor expressing GPC-1 in a subject, wherein the method comprising administering to the subject a nucleic acid that encodes a polypeptide comprising an extracellular domain capable of binding to glypican-1 (GPC-1), a transmembrane domain and one or more intracellular domains, wherein at least one of the intracellular domains is an intracellular domain comprising a primary cytosolic signaling sequence; wherein the extracellular domain capable of binding to GPC-1 comprises the heavy chain variable region (VH) and light chain variable region (VL) of anti-GPC-1 antibody and wherein the nucleotide sequence encoding the heavy chain variable region of anti-GPC-1 antibody comprises the nucleotide sequence listed as SEQ ID NO: I or a nucleotide sequence with at least 95% identity therewith and having the same function, and the nucleotide sequence encoding the light chain variable region comprises the nucleotide sequence listed as SEQ ID NO: 2 or a nucleotide sequence with at least 95% identity therewith and having the same function.

12. The method according to claim 11, wherein the solid tumor is squamous cell carcinoma, esophageal cancer or colon cancer.

* * * * *

SEQUENCE LISTING

```
<160> NUMBER OF SEQ ID NOS: 5

<210> SEQ ID NO 1
<211> LENGTH: 369
<212> TYPE: DNA
<213> ORGANISM: Artificial Sequence
<220> FEATURE:
<223> OTHER INFORMATION: heavy-chain variable region

<400> SEQUENCE: 1
gcggtgacgt tggacgagtc cgggggcggc ctccagacgc ccggaagagc gctcagcctc        60
gtctgtaagg cctccgggtt caccttcagc cgttacgcca tgtactgggt gcgacaggcg       120
cccggcaagg ggctggagtt cgtcgctggt attggcaaca ctggtagata cacaggctac       180
gggtcggcgg tgaagggccg tgccaccatc tcgagggaca gcgggcagag cacagtgagg       240
ctgcaactga acaacctcag ggctgaggac accggcaact actactgcgc caaaagtgtt       300
agtccttact gttgtgatgc tgctgacatc gacgcatggg gccacgggac cgaagtcatc       360
gtctcctcc                                                             369

<210> SEQ ID NO 2
<211> LENGTH: 318
<212> TYPE: DNA
<213> ORGANISM: Artificial Sequence
<220> FEATURE:
<223> OTHER INFORMATION: light-chain variable region

<400> SEQUENCE: 2
gctagcactc agccgtcctc ggtgtcagca aacccaggag aaaccgtcaa gatcacctgc        60
tccgggggta gcagtggcta tgcttatggc tggtaccagc agaagtctcc tggcagtgcc       120
cctgtcactc tgctctatag caacaacaac agaccctcgg acatcccttc acgattctcc       180
ggttccaaat ccggctccac agccacatta accatcactg gggtccaagc cgaggacgag       240
gctgtctatt tctgtgggag tgtagacagc agcagttatg ctggtatatt tggggccggg       300
acaaccctga ccgtccta                                                   318

<210> SEQ ID NO 3
<211> LENGTH: 123
<212> TYPE: PRT
<213> ORGANISM: Artificial Sequence
<220> FEATURE:
<223> OTHER INFORMATION: heavy-chain variable region

<400> SEQUENCE: 3

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Arg Tyr
            20                  25                  30
```

-continued

```
Ala Met Tyr Trp Val Arg Gln Ala Pro Gly Lys Gly Leu Glu Phe Val
        35                  40                  45

Ala Gly Ile Gly Asn Thr Gly Arg Tyr Thr Gly Tyr Gly Ser Ala Val
        50                  55                  60

Lys Gly Arg Ala Thr Ile Ser Arg Asp Ser Gly Gln Ser Thr Val Arg
65                  70                  75                  80

Leu Gln Leu Asn Asn Leu Arg Ala Glu Asp Thr Gly Asn Tyr Tyr Cys
                85                  90                  95

Ala Lys Ser Val Ser Pro Tyr Cys Cys Asp Ala Ala Asp Ile Asp Ala
                100                 105                 110

Trp Gly His Gly Thr Glu Val Ile Val Ser Ser
        115                 120
```

```
<210> SEQ ID NO 4
<211> LENGTH: 106
<212> TYPE: PRT
<213> ORGANISM: Artificial Sequence
<220> FEATURE:
<223> OTHER INFORMATION: light-chain variable region

<400> SEQUENCE: 4

Ala Ser Thr Gln Pro Ser Ser Val Ser Ala Asn Pro Gly Glu Thr Val
1               5                   10                  15

Lys Ile Thr Cys Ser Gly Gly Ser Ser Gly Tyr Ala Tyr Gly Trp Tyr
                20                  25                  30

Gln Gln Lys Ser Pro Gly Ser Ala Pro Val Thr Leu Leu Tyr Ser Asn
        35                  40                  45

Asn Asn Arg Pro Ser Asp Ile Pro Ser Arg Phe Ser Gly Ser Lys Ser
        50                  55                  60

Gly Ser Thr Ala Thr Leu Thr Ile Thr Gly Val Gln Ala Glu Asp Glu
65                  70                  75                  80

Ala Val Tyr Phe Cys Gly Ser Val Asp Ser Ser Ser Tyr Ala Gly Ile
                85                  90                  95

Phe Gly Ala Gly Thr Thr Leu Thr Val Leu
                100                 105
```

```
<210> SEQ ID NO 5
<211> LENGTH: 63
<212> TYPE: DNA
<213> ORGANISM: Artificial Sequence
<220> FEATURE:
<223> OTHER INFORMATION: Chemically synthesized lead sequence

<400> SEQUENCE: 5
atggccttac cagtgaccgc cttgctcctg ccgctggcct tgctgctcca cgccgccagg        60
ccg                                                                        63
```